(12) United States Patent
Brandestini

(10) Patent No.: US 8,074,496 B2
(45) Date of Patent: Dec. 13, 2011

(54) APPARATUS FOR HARDNESS MEASUREMENT BY IMPACT

(76) Inventor: Marco Brandestini, Schwerzenbach (CH)

( * ) Notice: Subject to any disclaimer, the term of this patent is extended or adjusted under 35 U.S.C. 154(b) by 634 days.

(21) Appl. No.: 11/993,657

(22) PCT Filed: Jun. 24, 2005

(86) PCT No.: PCT/CH2005/000352
§ 371 (c)(1),
(2), (4) Date: Jan. 19, 2009

(87) PCT Pub. No.: WO2006/136038
PCT Pub. Date: Dec. 28, 2006

(65) Prior Publication Data
US 2010/0192680 A1 Aug. 5, 2010

(51) Int. Cl.
*G01N 3/42* (2006.01)
*G01N 3/52* (2006.01)
*G06F 1/00* (2006.01)

(52) U.S. Cl. ................................. 73/79; 73/82; 713/323

(58) Field of Classification Search ........ 73/82; 173/90, 173/121
See application file for complete search history.

(56) References Cited

U.S. PATENT DOCUMENTS

| | | |
|---|---|---|
| 2,664,743 A | 1/1954 | Schmidt |
| 3,510,607 A * | 5/1970 | Getz et al. .................. 200/81 R |
| 3,576,127 A | 4/1971 | Weitzel et al. |
| 3,669,261 A | 6/1972 | Moulin |
| 3,879,982 A | 4/1975 | Schmidt |
| 4,034,603 A * | 7/1977 | Leeb et al. ....................... 73/79 |
| 4,411,153 A | 10/1983 | Lewis |
| 5,079,728 A | 1/1992 | Adams et al. |
| 5,176,026 A | 1/1993 | Leeb et al. |
| 5,827,953 A | 10/1998 | Sato et al. |
| 5,959,198 A | 9/1999 | Pollok et al. |
| 7,284,414 B2 * | 10/2007 | Wu ................................... 73/79 |
| 2001/0010170 A1 | 8/2001 | Sato et al. |

FOREIGN PATENT DOCUMENTS

| | | |
|---|---|---|
| AU | 677160 | 7/1992 |
| CN | 2039842 U | 6/1989 |
| DE | 3930483 | 3/1991 |
| DE | 19904448 | 8/2000 |
| FR | 1.001.230 | 2/1952 |
| GB | 737719 | 9/1955 |
| GB | 1092038 | 11/1967 |
| SU | 978010 | 11/1982 |
| WO | WO90-10857 | 9/1990 |
| WO | WO98-03848 | 1/1998 |

OTHER PUBLICATIONS

AAPA, Applicant's Admitted Prior Art, drawing Fig. 1, date: May 18, 2011.* Polvani, et al., A Dynamic Microindentation Apparatus for Materials Characterization, Journal of Testing & Evaluation 16 (Jan. 1988), No. 1, Philadelphia, PA USA, 12-16.

* cited by examiner

*Primary Examiner* — Lisa Caputo
*Assistant Examiner* — Roger Hernandez-Prewitt
(74) *Attorney, Agent, or Firm* — Marshall, Gerstein & Borun LLP

(57) ABSTRACT

The apparatus comprises an actuator (23) that can be pushed from an extended position to a depressed position. When doing so, the actuator (23) first releases an impact body (32) to impinge against the sample (2), and then a catcher (40, 42) to be moved to the released impact body (32) for bringing it back. The passage of the impact body (32) is detected by a reed switch (28), which wakes up the processing circuitry and switches the same between two modes of operation. In the first mode, the circuitry displays a device status, and in the second mode a measuring result.

15 Claims, 3 Drawing Sheets

APPARATUS FOR HARDNESS MEASUREMENT BY IMPACT

TECHNICAL FIELD

The invention relates to an apparatus for the hardness measurement of a sample by impacting an impact body against the sample and measuring a parameter of the rebound of the impact body.

BACKGROUND ART

In the field of non-destructive hardness testing a large variety of tests are being performed using impact devices. An original concept was described in U.S. Pat. No. 4,034,603.

To determine the hardness of the sample to be tested, the rebound energy is assessed in some fashion; either as an absolute value or in a ratiometric way by relating it to the inbound energy.

Typically these devices consist of a tubular housing and a cylindrical or bullet-shaped impact body that can move linearly inside the housing. To perform a test, the impact body impacts on the surface to be tested with a certain energy. The majority of the impact devices use a spring to supply the impact energy.

Attention is now drawn to the two most common mechanisms.

1) In a first class of devices, the handle or the body of the device is operated to charge the spring to a maximum pressure, upon which a trigger releases the impact body automatically. After the impact action, the device returns to its "relaxed" state by means of a second spring. This mode of operation is considered the classic mode, since we find it, among others, in tools such as spring-activated centrepunches or devices to set nails or staples. Similar mechanisms are also common to weapons.

2) In a second class of devices, the spring is charged to maximum spring pressure and the device is held in the armed state. A trigger is released by a separate operation, e.g. by depressing a button. This is the concept described in e.g. U.S. Pat. No. 4,034,603.

A brief analysis of the two modes shows their drawbacks with regard to the scope of the device which is subject of the invention.

In case 1) the operator is physically stressed when charging the loading spring (which can store a considerable energy). This leads to tremor and slippage, in other words to unreliable results.

In case 2) the above problem is alleviated—the operator can trigger the device in a relaxed fashion—however, at the expense of an additional operation and a separate mechanical trigger. In cases where the testing device is actuated by a robotic arm, an additional trigger means a more complicated, less agile system.

FIG. 1 shows a typical impact device used for the testing of metal hardness that operates according to case 2) described above.

This type of impact device has become the industry standard (ASTM report).

Let us analyze the charging and trigger features of the classic device, since these will be superceeded by the present invention.

To "arm" the device, the impact spring is loaded by manually pushing the loading tube 1 towards the sample 2. This operation will move the catch chuck 3 by means of the tubular carrier 4 and, when in the fully compressed position, catch the impact body 5 by its anchor pin. The loading spring 6 will subsequently retract the assembly to its home position, thereby arming the impact spring 7. Actuating an external trigger button 8 will, by means of the push rod 9 and its conical tip 10, open the catch chuck 3 and release the impact body 5.

The signal processing and indicating circuitry 11 is either located in a separate unit or mounted directly onto the impact device. The circuitry must be powered in order to detect the voltage induced in the pick-up coil 12 and indicate a hardness reading.

DISCLOSURE OF THE INVENTION

It is a first object of the invention to provide an apparatus that is easier to use.

Now, in order to implement this and still further objects, which will become more readily apparent as the description proceeds, the apparatus for a hardness measurement of a sample comprises a housing, an impact body to be impacted against said sample, wherein said impact body is moveable along an axis of said apparatus between a loaded position and a released position, an actuator movable along a path from an extended to a depressed position, wherein said device is adapted for triggering said impact body to be released from said loaded position by moving said actuator away from said extended position towards said depressed position and for moving said impact body from said released position to said loaded position by moving said actuator from said depressed position to said extended position, thus loading the device.

This type of apparatus allows to operate the device with a single motion, namely by moving the actuator. In contrast to conventional type 1 devices as mentioned above, however, the force to be exerted by the user while loading the apparatus can be much lower.

In a second aspect of the invention, an apparatus for hardness measurement of a sample is provided that comprises a housing, an impact body to be impacted against said sample, wherein said impact body is moveable along an axis of said apparatus between a loaded position and a released position, measuring circuitry for measuring a rebound of said impact body from said sample, a detector detecting a passage of said impact body at a location between said loaded position and said released position, wherein said measuring circuitry has a first and a second mode of operation, wherein the passage of said impact body at the location of said detector in a direction towards said released position switches said measuring circuitry to said second mode of operation and wherein the passage of said impact body at the location of said detector in a direction away from said released position switches said circuitry to said first mode of operation.

Hence, this apparatus uses the motion of the impact body to switch between two modes of operation, which e.g. allows to reduce the number of explicit commands the user has to give to the device, thereby allowing a reduction of interface elements and/or increased convenience and/or reliability.

In a particularly advantageous embodiment, the transition between the modes is detected by a reed switch that is actuated by the magnetic field of a magnet arranged in the impact body. Such a reed switch does not draw power and therefore allows a very low power stand-by operation of the circuitry.

The magnet can be the same magnet that is used in conventional apparatus to induce a current in the pick-up coil.

It is a further object of the invention to provide an apparatus with low power consumption. Hence, in a final aspect of the invention, the apparatus for the hardness measurement of a sample comprises an impact body to be impacted against said sample, wherein said impact body comprises a magnet and is moveable along an axis of said apparatus between a loaded position and a released position, measuring circuitry for measuring a rebound of said impact body from said sample, and a reed switch detecting a passage of said impact body at a location between said loaded position and said released position.

The reed switch can e.g. be used to wake up the circuitry from sleep mode or enable the transition between two modes of operation as mentioned above.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 2:
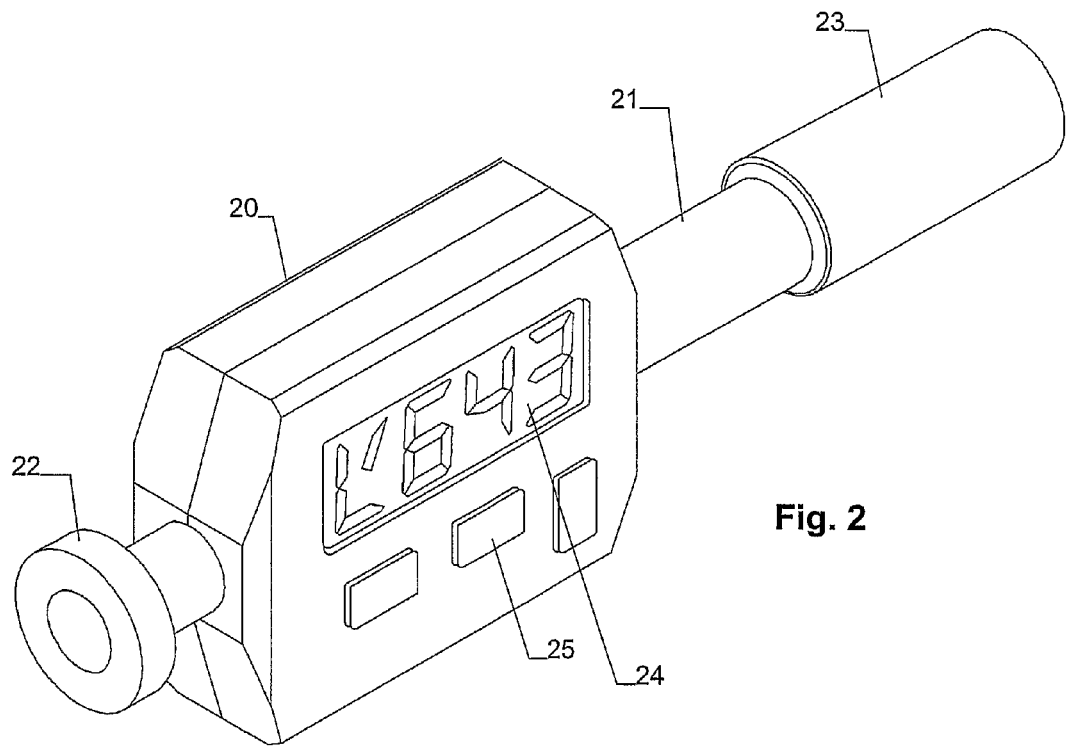
FIG. 2 shows a view of an advantageous embodiment of the invention.

A general view of an advantageous embodiment of the apparatus is shown in FIG. 2. It comprises a housing having a case 20 and a guide tube 21 extending through the case 20. A forward end of guide tube 21 carries a support ring 22, while an actuator 23 is slideably arranged at a rear end of guide tube 21. The actuator 23 forms a cylindrical handle to be gripped by the user. Case 20 holds measurement circuitry, a display 24 as well as user operatable input elements, such as push buttons 25.

Figure 3:
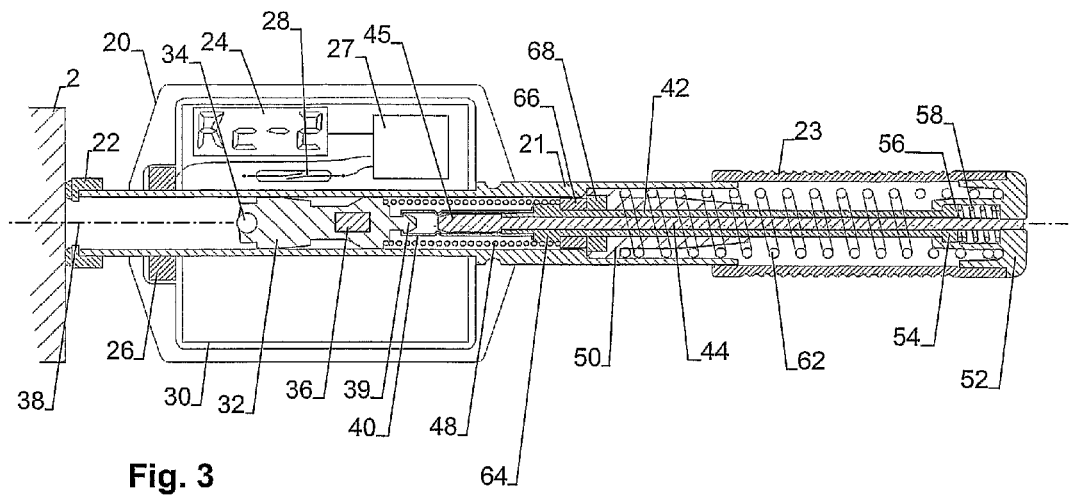
FIG. 3 shows the apparatus of FIG. 2 with the impact body in its loaded position.

Attention is now drawn to FIG. 3, which shows the design of the components within the apparatus.

The main structure of the device is the guide tube 21. The support ring 22 is arranged at the forward end of the guide tube 21, where the apparatus is in contact with the sample 2 to be tested. A pick-up coil 26 is wound around the guide tube 21 near its forward end within case 20.

For a compact device, i.e. a system where impact device and electronics are integrated into a single hand-held unit, the case 20 is mounted to the guide tube 21. It contains various circuitry, such as signal processor 27, the display 24 and the pick-up coil 26, as well as a reed switch 28 used as a detector. All of these components are placed on a circuit board 30.

The moving parts, from left to right are: An impact body 32 equipped with a hard tip 34 and carrying a magnet 36. The impact body 32 is arranged in guide tube 21 and slideable along an axis 38 thereof.

The interaction between magnet 36 and pick-up coil 26 is e.g. as described in U.S. Pat. No. 4,034,603 and allows to measure a parameter of the rebound process indicative of the hardness of the sample 2.

In its loaded position as shown in FIG. 3, a rear anchor pin 39 of the impact body 32 is engaged by a catcher. The catcher comprises a catch chuck 40 mounted to a tubular carrier 42. The catcher 40, 42 can be released by means of a release mechanism comprising a push-rod 44 with a conical tip 45. Catch chuck 40 is normally in the gripping position in which it is able to grip anchor pin 39; it can be opened to release the impact body 32 by means of the conical tip 45 that is part of the push-rod 44. The push-rod 44 extends from the actuator 23 to the catcher, is mounted coaxially to the tubular carrier 42 and its rear end is fastened to the actuator 23. In the embodiment of FIG. 2, push-rod 44 is slideably arranged within tubular carrier 42.

An impact spring 48 extends between the catcher and the impact body. When in the armed state with the impact body 32 in its loaded position, the impact spring 48 is fully compressed. Its forward end pushes against the impact body 32; its rear end is fastened to a threaded section of the tubular carrier 42.

The tubular carrier 42 is moveably guided by a center piece 50, which is rigidly connected to the guide tube 21.

At its rear end, the tubular carrier 42 is held in an end cap 52 of the actuator 23 by means of a widened section 54. The widened section 54 is pushed against a ledge 56 of the end cap 52 by means of a trigger spring 58.

The end cap 52 is connected to the actuator 23, which is the primary human interface of the apparatus, as described below.

A loading spring 62 extends between tubular guide 21 and the end cap 52 of actuator 23, pushing the actuator 23 to a fully extended position as shown in FIG. 3. Push-rod 44 holds the actuator 23 against the force of loading spring 62 because it is retained by a widened section 64 abutting against a ledge inside tubular guide 21.

Figure 1:
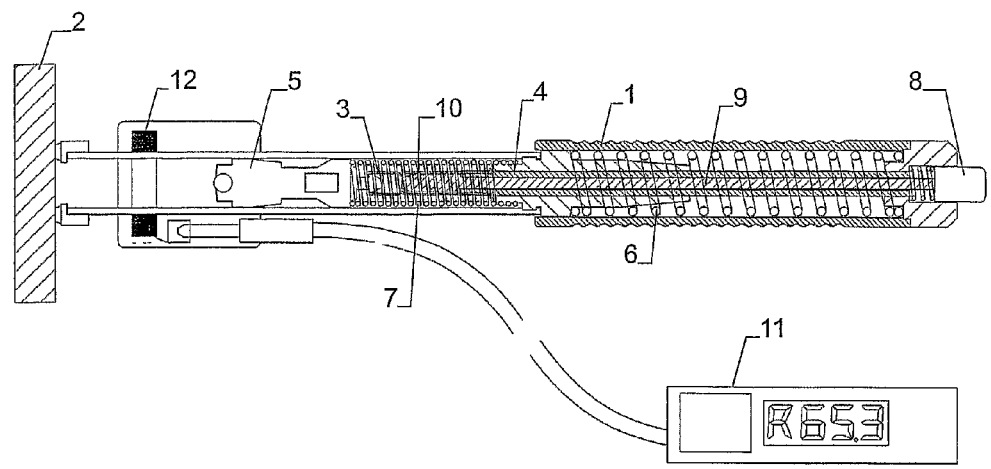
FIG. 1 is a prior art apparatus.

A look at FIG. 1 will show that for most part the elements of the assembly are identical or similar to those found in conventional impact devices. One difference is the lack of the release button 8 at the rear end and the presence of a coupling.

The purpose of this coupling is to hold the catcher 40, 42 in its first, rearward position as shown in FIG. 3, but to release it once that a force exceeding a trigger force acts on the catcher 40, 42 in forward direction along axis 38. The coupling comprises an annular yoke 66 fixedly mounted on tubular carrier 42. Yoke 66 is of a ferromagnetic material (such as soft iron or permalloy). It sits next to a magnetic ring 68, which is made from a strong magnetic material (such as rare earth-cobalt or neodymium-iron-boron). The magnetic ring 68 is mounted to the center piece 50.

The combination of the ferrous yoke 66 and the magnetic ring 68 forms a magnetic coupling that ensures that the catcher 40, 42 is firmly kept in is first, rearward position until the catch chuck 40 has opened and the impact body 32 has been released.

In a preferred embodiment of the invention the impact spring 48 is loaded, in the position as shown in FIG. 3, to 1.5 to 2 Newton. The trigger spring 58 is set to 2.5 to 3 Newton to ensure that the catch chuck 40 will not open under the force of the impact spring 48. The loading spring 62 can be rated as low as 5 Newton, which is a third of the ratings found in conventional push button-triggered units.

Note that in the conventional implementations (as shown in FIG. 1) the home position is assured by the loading spring 6 alone. This requires the loading spring 6 to be substantially harder than what would be needed to retract the impact body to the home position.

The reduced force of the loading spring 62 has an attractive benefit in the case of robotic testing. Small robots that can operate in the vicinity of human operators without a protecting cage are typically force-limited to 5 Newton. The inventive system can thus be designed to meet said requirement.

So far we have looked at the impact device in its armed state, i.e. with impact spring 48 compressed and impact body 32 is in its loaded position as shown in FIG. 3.

Figure 4:
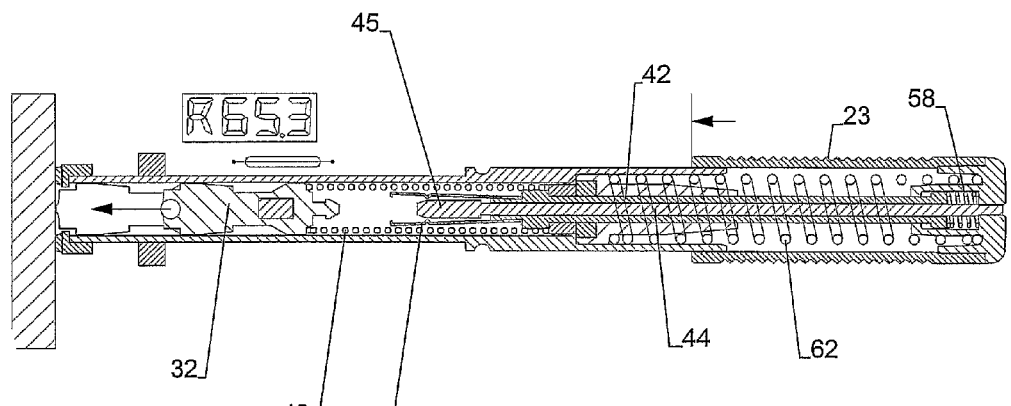
FIG. 4 shows the apparatus shortly after releasing the impact body.

Now let us look at the triggering operation depicted in FIG. 4.

The operator typically uses the apparatus in a two handed fashion. One hand ensures a steady position of the apparatus on the sample 2 by gripping the forward end of the guide tube 21 and/or the case 20. The other hand holds the actuator 23.

(In some applications the user may want to operate single handedly—this is also facilitated by the invention).

Pushing the actuator 23 away from its extended position forward along axis 38, i.e. towards the sample 2, the loading spring 62 and the trigger spring 58 will be compressed. Since the tubular carrier 42 is kept in its rearmost position by the combination of the ferrous yoke 66 and the magnetic ring 68, the push rod 44 will deform the catch chuck 40 to open it. The impact body 32 is released, the impact spring 48 extends to accelerate the impact body 32 against the sample 2, and a measurement is taken.

At this point the user can either let the actuator 23 return to its fully extended position or continue to push it forward.

Figure 5:
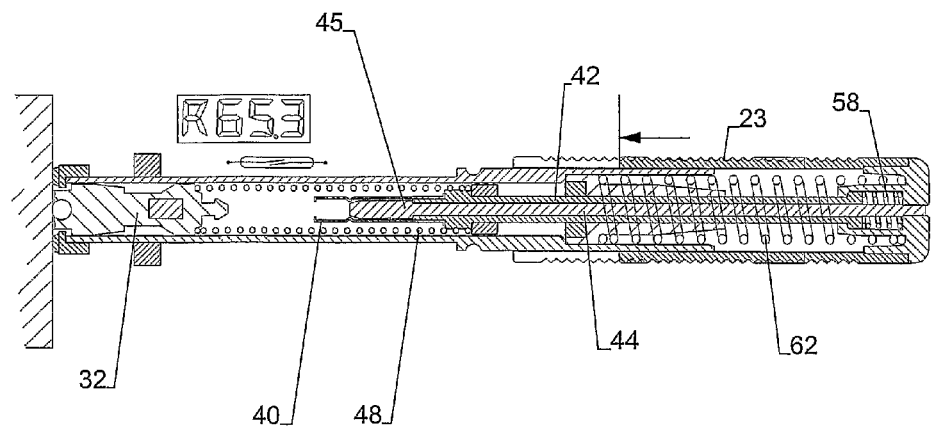
FIG. 5 shows the apparatus with the impact body in its released position.

When the actuator 23 is pushed forward further, the force that trigger spring 58 exerts on tubular carrier 42 will, at some time after the tip 45 has opened the catch chuck 40, exceed the trigger force of the magnetic coupling between yoke 66 and magnetic ring 68. At this point, the coupling will release the catcher 40, 42 to move together with actuator 23 along axis 38 (as shown in FIG. 5). In this way, the catcher can be brought to a forward, second position by moving actuator 23 to its fully depressed position. Here, catcher 40, 42 can engage the impact body 32, which now is in its released position as shown in FIG. 5.

Note that immediately after the coupling 66, 68 has been opened, the trigger spring 58 will expand again thus allowing the catch chuck 40 to close. In the drawings the rightmost section of the loading spring 62 is sectioned to highlight the state of the trigger spring 58.

Should the operator prefer to let the actuator 23 go to its extended position after releasing coupling 66, 68, a later pressure on the actuator 23 and exceeding the trigger force of the coupling 66, 68 will also allow to move the catcher forward to grip the impact body 32. (Obviously the unit will not trigger in this case.)

FIG. 5 shows an intermediate position of the actuator 23 with the catcher 40, 42 moving towards gripping the impact body 23. The catcher 40, 42 will engage the impact body 32 in its released position when the actuator 23 has been pushed in to its fully depressed position.

Figure 6:
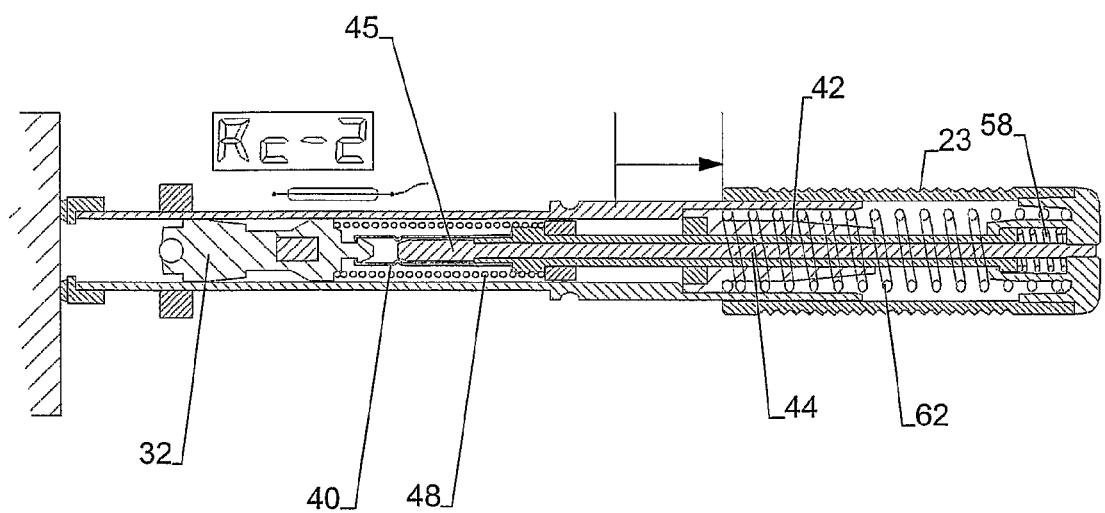
FIG. 6 shows the apparatus while the impact body is retracted from its released position.

FIG. 6 shows the apparatus after the catcher 40, 42 has gripped the impact body 32 and while loading spring 62 brings actuator 23, catcher 40, 42 and impact body 32 back to the loaded position.

For the sake of description we have chosen a magnetic coupling made up by the ferrous yoke 66 and the magnetic ring 68. A spring-type coupling mechanism would be an alternative with the similar features.

So far we have focussed on the mechanical part of the invention.

The idea of separating the armed and the relaxed state of the impact device allows for yet another important feature.

A modern, sub-miniature electronic indicating device is advantageously designed for lowest power consumption. Typically modern micro-controllers feature a "sleep" mode alleviating the use of an on/off switch. The question then arises how to wake the electronics with a device that does not draw any current when in the sleep mode. In the present embodiment this is accomplished by the reed switch 28, which is magnetically actuated by the magnet 36 that is part of the impact body 32. This is the same magnet 36 that is used to measure the velocity of the impact body 32 by means of the coil 26.

Sensing the transition of the impact body 32 in both directions, i.e. a) when about to impact on the sample 2 and b) when passing while being retracted to the home position, the reed switch 28 will close.

This event is used to wake up the circuitry and to perform two different tasks. a) If signal processor 27 detects that an impact signal is present after a pulse from the reed switch, i.e. a current is induced in pickup coil 26, the signal will be processed and a hardness value displayed on display 24; b) if processor 27 detects no impact signal after a pulse from the reed switch 28, i.e. no current is induced in pickup coil 26, it is assumed that the reed switch 28 has closed during a retraction of the impact device 32 and the processor 27 will cause the display 24 to indicate the settings of the apparatus rather than the last measurement.

This feature allows to share an indicating device with a few large characters, rather than requiring multiple rows that are hard to read, are of weaker contrast and more costly.

After having performed either task the circuitry will return to sleep mode.

In other words, the passage of the impact body 32 at the location of reed switch 28 will switch the circuitry between a first and a second mode of operation. In the first mode of operation, display 24 will display one or more settings of the device. In the second mode of operation, display 24 will display the result of the last measurement. When the impact body 32 passes at reed switch 28 on its way to the released position shown in FIG. 5, the circuitry will switch to the second mode of operation. When the impact body 32 passes at reed switch 28 when it is moved away from the released position, the circuitry will switch back to its first mode of operation.

To illustrate the time-shared mode of the display, in FIGS. 3 and 6 the display indicates that the apparatus has been set to read in the "Rockwell C" scale for cold work steel (material number 2). FIGS. 4 and 5, which show the apparatus after the impact, the display 24 indicates the measured hardness, in this case "65.3" Rockwell.

In addition to switching the circuitry between its two modes of operation, reed switch 28 has the further purpose to wake the circuitry up from sleep. Each time switch 28 is actuated, processor 27 starts processing in active mode with high power consumption, either to perform a measurement and display its result, or to retrieve the current settings and display them. Once that task is finished, processor 27 will go back to sleep mode with low power consumption.

Hence, as can be seen, reed switch 28 serves two different purposes that can be used in combination or alone: a) it allows to switch the circuitry between the two modes of operations; b) it wakes the circuitry from sleep mode.

Regarding the electric part of the invention the magnetically actuated reed switch 28 could be replaced by any type of detector actuated by the impact body 32 or any other moving part of the impact device.

While there are shown and described presently preferred embodiments of the invention, it is to be distinctly understood that the invention is not limited thereto but may be otherwise variously embodied and practiced within the scope of the following claims.

The invention claimed is:

1. An apparatus for hardness measurement of a sample, said apparatus comprising
a housing,
an impact body to be impacted against said sample, wherein said impact body is moveable along an axis of said apparatus between a loaded position and a released position,
an actuator movable along a path from an extended to a depressed position,
wherein said device is adapted
for triggering said impact body to be released from said loaded position by moving said actuator away from said extended position towards said depressed position and
for moving said impact body from said released position to said loaded position by moving said actuator from said depressed position to said extended position
said apparatus further comprising
a catcher operatable by said actuator to engage said impact body in said released position when said actuator is moved to said depressed position and to hold said impact body in said loaded position when said actuator is in said extended position,
a release mechanism operatable by said actuator for releasing said impact body from said catcher when said actuator is moved away from said extended position towards said depressed position, and
a coupling holding said catcher in a first position, wherein, upon exertion of a trigger force along said axis exceeding a coupling force, said coupling releases said catcher to move along said axis towards a second position where it can engage said impact body.

2. The apparatus of claim 1 wherein said coupling is a magnetic coupling.

3. The apparatus of claim 1 wherein said release mechanism comprises a push-rod extending from said actuator to said catcher, wherein said push rod is adapted to deform said catcher to release said impact body from said catcher when said catcher is in said first position and said actuator is moved away from said extended position towards said depressed position.

4. The apparatus of claim 3 further comprising a trigger spring (58) arranged between said catcher and said actuator, wherein, when said actuator is moved away from said extended position towards said depressed position, said push rod first deforms said catcher to release said impact body and only then said trigger spring exerts a force exceeding said trigger force for opening said coupling.

5. The apparatus of claim 3 wherein said catcher and said push rod are arranged coaxially.

6. The apparatus of claim 5 wherein said catcher comprises a tubular carrier and wherein said push rod is slideably arranged within said tubular carrier.

7. The apparatus claim 1 further comprising an impact spring extending between said catcher and said impact body, wherein, when said impact body is released from said loaded position, said impact spring extends to accelerate said impact body against said sample.

8. The apparatus of claim 1 further comprising a loading spring extending between said housing and said actuator for pushing said actuator towards said extended position.

9. The apparatus of claim 1 wherein said actuator forms a handle to be gripped by the user.

10. An apparatus for hardness measurement of a sample, said apparatus comprising
a housing,
an impact body to be impacted against said sample, wherein said impact body is moveable along an axis of said apparatus between a loaded position and a released position,
measuring circuitry for measuring a rebound of said impact body from said sample,
a detector detecting a passage of said impact body at a location between said loaded position and said released position,
wherein said measuring circuitry has a sleep mode with low power consumption and an active mode with high power consumption, and wherein a signal from said detector switches said circuitry to the active mode.

11. The apparatus of claim 10 further comprising a magnet arranged in said impact body, wherein said detector is a reed switch actuated by said magnet.

12. The apparatus of claim 11 further comprising a coil arranged along a path of said impact body, wherein said measuring circuitry is adapted to measure a parameter of said rebound from a current induced by said magnet in said coil.

13. The apparatus of claim 12 wherein said measuring circuitry switches to said second mode of operation if a pulse from said reed switch is followed by a current pulse in said coil and switches to said first mode of operation if not.

14. The apparatus of claim 10 further comprising a display, wherein, in said first mode of operation, said circuitry is adapted to display a setting of said apparatus on said display in said first mode of operation and a measurement result in said second mode of operation.

15. An apparatus for hardness measurement of a sample, said apparatus comprising
an impact body to be impacted against said sample, wherein said impact body comprises a magnet and is moveable along an axis of said apparatus between a loaded position and a released position,
measuring circuitry for measuring a rebound of said impact body from said sample, and
a reed switch detecting a passage of said impact body at a location between said loaded position and said released position,
wherein said measuring circuitry has a sleep mode with low power consumption and an active mode with high power consumption, and wherein a signal from said detector switches said circuitry to the active mode.

* * * * *

UNITED STATES PATENT AND TRADEMARK OFFICE
CERTIFICATE OF CORRECTION

| | | |
|---|---|---|
| PATENT NO. | : 8,074,496 B2 | Page 1 of 1 |
| APPLICATION NO. | : 11/993657 | |
| DATED | : December 13, 2011 | |
| INVENTOR(S) | : Brandestini | |

It is certified that error appears in the above-identified patent and that said Letters Patent is hereby corrected as shown below:

In the Claims

Column 7, Line 48, Claim 4, delete "spring (58)" and insert -- spring --, therefor.

Column 8, Line 1, Claim 7, delete "apparatus claim" and insert -- apparatus of claim --, therefor.

Signed and Sealed this
Thirtieth Day of September, 2014

Michelle K. Lee
*Deputy Director of the United States Patent and Trademark Office*